(12) United States Patent
Gambale

(10) Patent No.: US 7,204,847 B1
(45) Date of Patent: Apr. 17, 2007

(54) IMPLANT ANCHOR SYSTEMS

(75) Inventor: Richard A. Gambale, Tyngsboro, MA (US)

(73) Assignee: C. R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 10/048,205

(22) PCT Filed: Jul. 28, 2000

(86) PCT No.: PCT/US00/20574

§ 371 (c)(1),
(2), (4) Date: May 2, 2002

(87) PCT Pub. No.: WO01/08602

PCT Pub. Date: Feb. 8, 2001

(51) Int. Cl.
*A61F 2/06* (2006.01)

(52) U.S. Cl. .................. 623/1.14; 623/1.22

(58) Field of Classification Search ........... 623/1.11, 623/1.15–1.22, 1.32–1.37, 904, 910; 606/108
See application file for complete search history.

(56) References Cited

U.S. PATENT DOCUMENTS

| | | | |
|---|---|---|---|
| 3,991,750 | A | 11/1976 | Vickery |
| 3,995,617 | A | 12/1976 | Watkins et al. |
| 4,307,722 | A | 12/1981 | Evans et al. |
| 4,503,569 | A | 3/1985 | Dotter |
| 4,546,499 | A | 10/1985 | Possis |
| 4,562,597 | A | 1/1986 | Possis et al. |
| 4,580,568 | A | 4/1986 | Gianturco |
| 4,582,181 | A | 4/1986 | Samson |
| 4,641,653 | A | 2/1987 | Rockey |
| 4,649,922 | A | 3/1987 | Wiktor |
| 4,655,771 | A | 4/1987 | Wallsten |
| 4,658,817 | A | 4/1987 | Hardy |
| 4,665,918 | A | 5/1987 | Garza et al. |

(Continued)

FOREIGN PATENT DOCUMENTS

DE 19703482 1/1997

(Continued)

OTHER PUBLICATIONS

U.S. Appl. No. 09/073,118, filed May 5, 1998, Gambale.

(Continued)

*Primary Examiner*—Suzette Gherbi
(74) *Attorney, Agent, or Firm*—Kirkpatrick & Lockhart Preston Gates Ellis LLP

(57) ABSTRACT

The present invention provides implant devices configured to become anchored within tissue so that they do not migrate despite experiencing aggressive migration forces applied by the highly dynamic movement of muscle tissue that surrounds them. Additionally, methods for placing the devices so that they remain securely anchored within the tissue are provided. The devices are comprised of a flexible body, preferably formed from a helical wound spring. In a preferred embodiment the spring is wound from a ribbon-like filament having series of barbs or ridges formed along the proximal facing edge of the wound ribbon. The ribbon-like filament may be etched from a flat sheet of material, having barbs formed along one edge. The filament may then be wrapped into a helical coil shape to take the form of an implant having barbs formed along the proximally facing edge of each coil to resist migration.

16 Claims, 3 Drawing Sheets

U.S. PATENT DOCUMENTS

| | | |
|---|---|---|
| 4,681,110 A | 7/1987 | Wiktor |
| 4,733,665 A | 3/1988 | Palmaz |
| 4,768,507 A | 9/1988 | Fischell et al. |
| 4,774,949 A | 10/1988 | Fogarty |
| 4,813,925 A | 3/1989 | Anderson, Jr. et al. |
| 4,861,330 A | 8/1989 | Voss |
| 4,889,137 A | 12/1989 | Kolobow |
| 4,904,264 A | 2/1990 | Scheunemann |
| 4,917,666 A | 4/1990 | Solar |
| 4,920,980 A | 5/1990 | Jackowski |
| 4,950,227 A | 8/1990 | Savin et al. |
| 4,995,857 A | 2/1991 | Arnold |
| 4,997,431 A | 3/1991 | Isner et al. |
| 5,040,543 A | 8/1991 | Badera et al. |
| 5,042,486 A | 8/1991 | Pfeiler et al. |
| 5,047,028 A | 9/1991 | Qian |
| 5,049,138 A | 9/1991 | Chevalier et al. |
| 5,056,517 A | 10/1991 | Fenici |
| 5,087,243 A | 2/1992 | Avitall |
| 5,092,877 A * | 3/1992 | Pinchuk ..................... 128/898 |
| 5,098,374 A | 3/1992 | Othel-Jacobsen et al. |
| 5,114,414 A | 5/1992 | Buchbinder |
| 5,158,548 A | 10/1992 | Lau et al. |
| 5,167,614 A * | 12/1992 | Tessmann et al. ......... 623/1.15 |
| 5,176,626 A | 1/1993 | Soehendra |
| 5,180,366 A | 1/1993 | Woods |
| 5,190,058 A | 3/1993 | Jones et al. |
| 5,256,146 A | 10/1993 | Ensminger et al. |
| 5,266,073 A | 11/1993 | Wall |
| 5,287,861 A | 2/1994 | Wilk |
| 5,290,678 A | 3/1994 | Jackowski |
| 5,312,456 A | 5/1994 | Reed et al. |
| 5,324,325 A | 6/1994 | Moaddeb |
| 5,366,493 A | 11/1994 | Scheiner et al. |
| 5,370,683 A | 12/1994 | Fontaine |
| 5,372,600 A | 12/1994 | Beyar et al. |
| 5,380,316 A | 1/1995 | Aita et al. |
| 5,389,096 A | 2/1995 | Aita et al. |
| 5,391,199 A | 2/1995 | Ben-Haim |
| 5,409,004 A | 4/1995 | Sloan |
| 5,409,019 A | 4/1995 | Wilk |
| 5,423,885 A | 6/1995 | Williams |
| 5,425,757 A | 6/1995 | Tiefenbrun et al. |
| 5,429,144 A | 7/1995 | Wilk |
| 5,441,516 A | 8/1995 | Wang et al. |
| 5,452,733 A | 9/1995 | Sterman |
| 5,453,090 A | 9/1995 | Martinez et al. |
| 5,458,615 A | 10/1995 | Klemm |
| 5,464,404 A | 11/1995 | Abela et al. |
| 5,464,650 A | 11/1995 | Berg et al. |
| 5,466,242 A | 11/1995 | Mori |
| 5,476,505 A | 12/1995 | Limon |
| 5,480,422 A | 1/1996 | Ben-Haim |
| 5,487,739 A | 1/1996 | Aebischer et al. |
| 5,514,176 A | 5/1996 | Bosley, Jr. et al. |
| 5,551,427 A | 9/1996 | Altman |
| 5,551,954 A | 9/1996 | Buscemi et al. |
| 5,562,619 A | 10/1996 | Mirarchi et al. |
| 5,562,922 A | 10/1996 | Lambert |
| 5,569,272 A | 10/1996 | Reed et al. |
| 5,571,168 A | 11/1996 | Toro |
| 5,593,412 A | 1/1997 | Martinez et al. |
| 5,593,434 A | 1/1997 | Williams |
| 5,602,301 A | 2/1997 | Field |
| 5,607,445 A * | 3/1997 | Summers ................... 623/1.22 |
| 5,614,206 A | 3/1997 | Randolph et al. |
| 5,643,308 A | 7/1997 | Markman |
| 5,653,756 A | 8/1997 | Clarke et al. |
| 5,655,548 A | 8/1997 | Nelson |
| 5,662,124 A | 9/1997 | Wilk |
| 5,676,850 A | 10/1997 | Reed |
| 5,690,643 A | 11/1997 | Wijay |
| 5,709,692 A * | 1/1998 | Mollenauer et al. ........ 606/141 |
| 5,735,897 A | 4/1998 | Buirge |
| 5,741,330 A | 4/1998 | Brauker et al. |
| 5,744,515 A | 4/1998 | Clapper |
| 5,755,682 A | 5/1998 | Knudson et al. |
| 5,756,127 A | 5/1998 | Grisoni et al. |
| 5,762,600 A | 6/1998 | Bruchman et al. |
| 5,769,843 A | 6/1998 | Abela et al. |
| 5,782,823 A | 7/1998 | Mueller |
| 5,785,702 A | 7/1998 | Murphy-Chutorian et al. |
| 5,792,453 A | 8/1998 | Hammond et al. |
| 5,797,870 A | 8/1998 | March et al. |
| 5,807,384 A | 9/1998 | Mueller |
| 5,810,836 A | 9/1998 | Hussein |
| 5,824,071 A | 10/1998 | Nelson et al. |
| 5,830,502 A | 11/1998 | Dong et al. |
| 5,833,699 A | 11/1998 | Chuter |
| 5,840,059 A | 11/1998 | March et al. |
| 5,868,780 A * | 2/1999 | Lashinski et al. ........... 606/198 |
| 5,899,915 A | 5/1999 | Saadat |
| 5,971,993 A | 10/1999 | Hussein et al. |
| 5,980,514 A | 11/1999 | Kupiecki et al. |
| 5,980,548 A | 11/1999 | Evans et al. |
| 6,019,779 A * | 2/2000 | Thorud et al. .............. 606/198 |
| 6,053,924 A | 4/2000 | Hussein |
| 6,053,943 A * | 4/2000 | Edwin et al. ............... 623/1.25 |
| 6,197,324 B1 | 3/2001 | Crittenden |
| 6,248,112 B1 | 6/2001 | Gambale et al. |
| 6,251,418 B1 | 6/2001 | Ahern et al. |
| 6,263,880 B1 | 7/2001 | Parker et al. |
| 6,277,082 B1 | 8/2001 | Gambale |
| 6,364,904 B1 * | 4/2002 | Smith ........................ 623/1.22 |
| 6,425,915 B1 * | 7/2002 | Khosravi et al. ........... 623/1.22 |
| 6,432,126 B1 | 8/2002 | Gambale et al. |
| 6,447,522 B2 | 9/2002 | Gambale et al. |
| 6,458,092 B1 | 10/2002 | Gambale et al. |
| 6,478,818 B1 * | 11/2002 | Taheri ........................ 623/1.36 |
| 6,491,707 B2 * | 12/2002 | Makower et al. ........... 606/157 |
| 6,494,657 B2 * | 12/2002 | Unsworth et al. .......... 411/412 |
| 6,494,907 B1 * | 12/2002 | Bulver ....................... 623/1.22 |
| 6,500,172 B1 * | 12/2002 | Panescu et al. .............. 606/31 |
| 6,544,275 B1 | 4/2003 | Teoh .......................... 606/158 |
| 6,620,170 B1 * | 9/2003 | Ahern ........................ 606/108 |

FOREIGN PATENT DOCUMENTS

| | | |
|---|---|---|
| DE | 296 19 029 U1 | 4/1997 |
| EP | 0 490 459 A1 | 6/1992 |
| EP | 0 515 867 A2 | 12/1992 |
| EP | 0 714 640 A1 | 6/1996 |
| EP | 0 717 969 A1 | 6/1996 |
| EP | 0 732 089 A2 | 9/1996 |
| EP | 0 812 574 A2 | 12/1997 |
| EP | 0 830 873 A2 | 3/1998 |
| EP | 0 876 803 A2 | 11/1998 |
| EP | 0 953 320 A2 | 11/1999 |
| FR | 1.514.319 | 1/1967 |
| FR | 2 725 615 | 10/1994 |
| RU | 2026640 C1 | 1/1995 |
| RU | 2063179 C1 | 7/1996 |
| WO | WO 89/01798 | 3/1989 |
| WO | WO 91/15254 | 10/1991 |
| WO | WO 94/05265 | 3/1994 |
| WO | WO 95/33511 | 12/1995 |
| WO | WO 96/20698 | 7/1996 |
| WO | WO 97/32551 | 9/1997 |
| WO | WO 97/44071 | 11/1997 |
| WO | WO 97/45105 | 12/1997 |
| WO | WO 97/47253 | 12/1997 |
| WO | WO 98/05307 | 2/1998 |
| WO | WO 98/08456 | 3/1998 |
| WO | WO 98/16644 | 4/1998 |

| WO | WO 98/23228 | 6/1998 |
| WO | WO 98/25533 | 6/1998 |
| WO | WO 98/29148 | 7/1998 |
| WO | WO 98/32859 | 7/1998 |
| WO | WO 98/46115 | 10/1998 |
| WO | WO 99/21510 | 5/1999 |
| WO | WO 99/38459 | 9/1999 |
| WO | WO 99/53863 | 10/1999 |

OTHER PUBLICATIONS

U.S. Appl. No. 09/159,834, filed Sep. 24, 1998, Cafferata.
U.S. Appl. No. 09/162,547, filed Sep. 29, 1998, Gambale.
U.S. Appl. No. 09/211,332, filed Dec. 15, 1998, Gambale et al.
U.S. Appl. No. 09/299,795, filed Apr. 26, 1999, Ahern.
U.S. Appl. No. 09/328,808, filed Jun. 9, 1999, Ahern.
U.S. Appl. No. 09/368,119, filed Aug. 4, 1999, Tedeschi et al.
U.S. Appl. No. 09/743,695, filed Apr. 12, 2001, Weiser et al.
U.S. Appl. No. 09/743,726, filed Apr. 12, 2001, Gambale et al.
U.S. Appl. No. 09/774,319, filed Jan. 31, 2001, Gambale et al.
U.S. Appl. No. 09/774,320, filed Jan. 31, 2001, Gambale et al.
U.S. Appl. No. 09/888,757, filed Jun. 25, 2001, Ahern et al.
U.S. Appl. No. 09/990,644, filed Nov. 21, 2001, Gambale et al.
U.S. Appl. No. 10/048,694, filed Jun. 10, 2002, Gambale et al.
A. Hassan Khazei et al., *Myocardial Canalization, A New Method of Myocardial Revascularization*, The Annals of Thoracic Surgery, vol. 6, No. 2, pp. 163-171, Aug. 1968.
Alfred Goldman et al., *Experimental Methods for Producing a Collateral Circulation to the Heart Directly from the Left Ventricle*, Journals of Thoracic Surgery, vol. 31, No. 3, pp. 364-374, Mar. 1956.
A. Sachinopoulou et al., *Invited Review Transmyocardial Revascularization*, Lasers in Medical Science 1995, vol. 10, pp. 83-91, Sep. 1995.
B. Schumacher, *Induction of Neoangiogenesis in Ischemic Myocardium by Human Growth Factors, First Clinical Results of a New Treatment of Coronary Heart Disease*, Clinical Investigation and Reports, pp. 645-650, Dec. 1997.
Charles T. Doiter, *Transluminally-placed Coilspring Endarterial Tube Grafts, Long-term Patency in Canine Popliteal Artery*, Investigative Radiology, pp. 329-332, Sep.-Oct. 1969.
C. Massimo, et al., *Myocardial Revascularization By a New Method of Carrying Blood Directly from the Left Ventricular Cavity into the Coronary Circulation*, Journals of Thoracic Surgery, vol. 34, No. 2, pp. 257-264, Aug. 1957.
Garrett Lee et al., *Feasibility of Intravascular Laser Irradiation for In Vivo Visualization and Therapy of Cardiocirculatory Diseases*, American Heart Journal, vol. 103, No. 6, pp. 1076-1077.
Garrett Lee et. al., *Laser-Dissolution of Coronary Atherosclerotic Obstruction*, American Heart Journal, vol. 102, No. 6, part 1, pp. 1074-1075, Dec. 1981.
George S. Abela et al., *Use of Laser Radiation to Recanalize Totally Obstructed Coronary Arteries(Abstract)*, Journal American College Cardiology 1983:1(2):691.
George S. Abela et al., *Laser Revascularization: What Are Its Prospects?*, Journal of Cardiovascular Medicine, pp. 977-984, Sep. 1983.

Isam N. Anabtawi et al., *Experimental Evaluation of Myocardial Tunnelization as a Method of Myocardial Revascularization*, Journal of Thoracic and Cardiovascular Surgery, vol. 58, No. 5, pp. 638-646, Nov. 1969.
John E. Hershey et al., *Transmyocardial Puncture Revascularization*, Geriatrics, pp. 101-108, Mar. 1969.
Ladislav Kuzela et al., *Experimental Evaluation of Direct Transventricular Revascularization*, Journal of Thoracic Cardiovascular Surgery, vol. 57, No. 6, pp. 770-773, Jun. 1969.
Mahmood Mirhoseini et al., *Myocardial Revascularization by Laser: A Clinical Report*; Lasers in Surgery and Medicine 3: 241-245 (1983).
Mahmood Mirhoseini et al., *Revascularization of the Heart by Laser*; Journal of Microsurgery, pp. 253-260, Jun. 1981.
Mahmood Mirhoseini et al., *Transventricular Revascularization by Laser*, Lasers in Surgery and Medicine, vol. 2, pp. 187-198, 1982.
Mahmood Mirhoseini et al., *Clinical Report: Laser Myocardial Revascularization*, Lasers in Surgery and Medicine vol. 6, pp. 459-461, 1986.
Mahmood Mirhoseini et al., *New Concepts in Revascularization of the Myocardium*, The Annals of Thoracic Surgery, vol. 45, No. 4, pp. 415-420, Apr. 1988.
Neil B. Ingels, et al., *Measurement of Midwall Myocardial Dynamics in Intact Man by Radiography of Surgically Implanted Markers*, Circulation, vol. 52, pp. 859-867 (Nov. 1975).
P. Walter et al., *Treatment of Acute Myocardial Infarction by Transmural Blood Supply from the Ventricular Cavity*, Department of Surgery and Department of Radiology of the Hannover Medical School, Hanover, pp. 130-138, (1971).
Peter Whittaker, et al., *Transmural Channels Can Protect Ischemic Tissue, Assessment of Long-term Myocardial Response to Laser and Needle-Made Channels*, Circulation, vol. 93, No. 1, pp. 143-152, Jan. 1996.
P.K. Sen, et al., *Further Studies in Multiple Transmyocardial Acupuncture as a Method of Myocardial Revascularization*, Surgery, vol. 64, No. 5, pp. 861-870, Nov. 1968.
P.K. Sen et al, *Transmyocardial Acupuncture, A New Approach to Myocardial Revascularization*; Journal of Thoracic and Cardiovascular Surgery, vol. 50, No. 2, pp. 181-189, Aug. 1965.
R.I. Hardy et al., *Regional Myocardial Blood Flow and Cardiac Mechanics in Dog Hearts with $CO_2$Laser-Induced Intramyocardial Revascularization*, Basic Research Cardiology, 85:179-197 (1990).
Roque Pifarre et al., *Myocardial Revascularization by Transmyocardial Acupuncture: A Physiologic Impossibility*; Journal of Thoracic and Cardiovascular Surgery; vol. 58, No. 3, pp. 424-429, Sep. 1969.
Valluvan Jeevanandam et l., *Myocardial Revascularization by Laser-Induced Channels*, Surgical Forum Vo. IVL, American College of Surgeons 76th Clinical Congress, vol. 4, pp. 225-227, Oct. 1990.

* cited by examiner

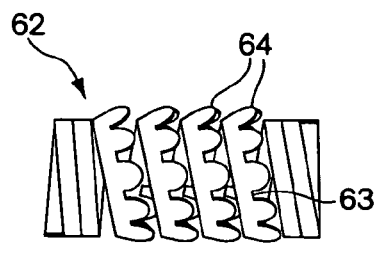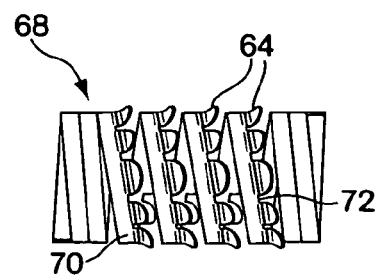
Fig. 4     Fig. 5
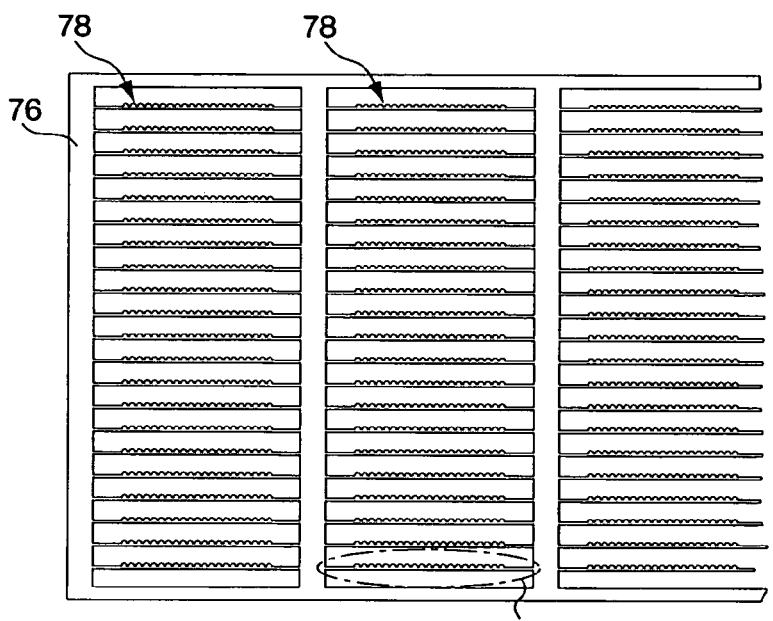
Fig. 6
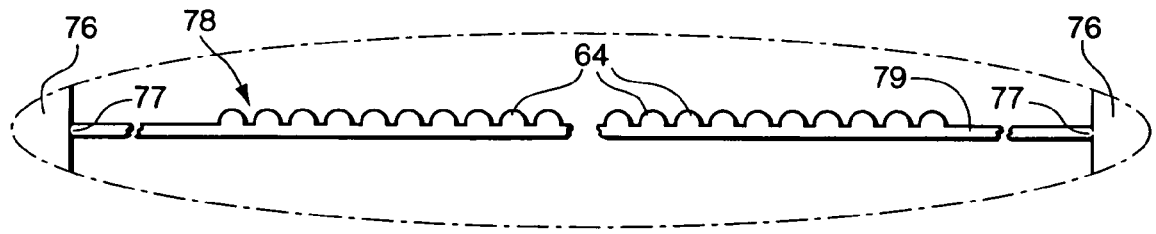
Fig. 7

IMPLANT ANCHOR SYSTEMS

FIELD OF THE INVENTION

This invention relates to tissue implant devices and methods of their use. In particular, the devices and methods concern systems for anchoring the implants in tissue so that they do not migrate after implantation.

BACKGROUND OF THE INVENTION

There are a variety of applications for tissue implant devices in the human body. Such applications include electrical pacing leads or other tissue monitoring devices or tissue support structures such as endoluminal stents. A device implanted in tissue may experience migratory forces applied by movement of the surrounding tissue into which the device has been implanted. Migration is especially a problem in muscle tissue that regularly contracts and relaxes around the device. Because the device is static and is relatively inflexible, rather than absorbing the forces applied by the tissue, those forces act on the device to move it in the tissue. Migration of the device ultimately may lead to ejection of the device from the tissue. An ejected device could prove harmful to a patient if it enters the blood stream and blocks blood flow to a critical organ such as the brain.

Perhaps the most regular aggressive migratory forces created by muscle tissue may be experienced by implant devices which are placed in heart tissue. Because the heart muscle regularly contracts and relaxes in an exaggerated fashion to pump blood through the ventricle, implant devices located within that tissue have significant forces applied upon them. For example, the myocardial tissue comprising the exterior wall of the heart at the left ventricle may increase in thickness by forty to sixty percent with each contraction. Conventional methods of anchoring a device to tissue such as by stapling or suturing prove difficult in applications where there is exaggerated and constant movement of the subject tissue because it is difficult to accurately apply a suture or staple to the intended location.

Implant devices for the heart have been disclosed in U.S. Pat. No. 5,429,144 (Wilk) and in U.S. Pat. No. 5,810,836 (Hussein et al.) for the purpose of restoring blood flow to the tissue of the heart. Conventional treatments of restoring blood flow to heart tissue such as coronary artery bypass grafting have been supplanted in recent years by various methods of transmyocardial revascularization (TMR). TMR methods include creating channels into tissue of the heart either by needle acupuncture or coring with a hypodermic tube or by laser or mechanical ablative methods. Hussein and Wilk attempt to maintain the patency of such channels by a placement of a mechanical implant device to the heart tissue to support an open pathway through which blood may flow. The Hussein patent discloses several stent embodiments that are delivered through the epicardium of the heart into the myocardium and positioned to be open to the left ventricle.

Due to the exaggerated migration forces experienced by an implant device in heart tissue as described above, it would be desirable to provide devices and methods for securely anchoring an implant in an associated dynamic region of tissue. It is a general object of the present invention to provide such an anchoring system for tissue implants, especially those intended for placement in the heart that may be useful for revascularization of the heart tissue by various mechanisms.

SUMMARY OF THE INVENTION

The present invention provides implant devices configured to become anchored within tissue so that they do not migrate despite experiencing aggressive migration forces applied by the highly dynamic movement of muscle tissue that surrounds them. Additionally, methods for placing the devices so that they remain securely anchored within the tissue are provided. The devices are comprised of a flexible body, preferably formed from a helical wound spring. In a preferred embodiment the spring is wound from a ribbon-like filament having series of barbs or ridges formed along the proximal facing edge of the wound ribbon.

The devices of the present invention may be delivered to the intended tissue location percutaneously, through a catheter based system, transthoracically or surgically. Although the inventive devices and methods can be applied to implants intended for use in any region of the body, it is believed that the anchor systems are especially useful as applied to implant devices for the heart configured to treat ischemia. Flexible implant devices may be configured to promote angiogenesis through a variety of mechanisms examples of which are described in detail in pending U.S. patent application Ser. Nos. 09/164,173, 09/211,332 and 09/299,795.

Generally, the spring implant devices may be considered to have a body having proximal and distal portions. In the present application, proximal is understood to mean the direction leading external to the patient and distal is understood to mean any direction leading internally to the patient. The implant devices discussed herein are delivered into the tissue in a distal direction so that the body is implanted within the tissue and the proximal end of the device is approximately flush with the tissue surface or slightly submerged under the surface. The configuration of the barbs resists migration of the device proximally back out of the tissue. Additionally, the barbs may serve to resist rotational movement of the device so that it does not "unscrew" out of the tissue.

In an embodiment of the invention, a flexible implant device formed from a helical spring body may be formed from a filament having a non-circular cross-section. For example, a filament having a rectangular cross-section may serve to prevent migration through the tissue in the axial direction by several mechanisms. When the helical coil is wound such that the major axis of the rectangular cross-section is substantially perpendicular to the longitudinal axis of the body of the device greater axial flexibility is imparted to the spring, while maintaining sufficient radial stiffness to resist crushing by the tissue, than would be possible with a round cross-sectional filament material. Increased axial flexibility of the device permits it to move with surrounding tissue, absorbing forces that would otherwise tend to push the device out of position in the tissue. Additionally, as surrounding tissue herniates through the individual coils of the device, the orientation of the major axis of the rectangular cross-section of the filament to be perpendicular to the longitudinal axis of the device presents a larger surface area engaging the tissue to resist axial migration.

Alternatively, the major axis of the rectangular cross-section filament may be oriented at an angle that is acute to the longitudinal axis of the device, so that the filament is canted in the proximal direction, to facilitate insertion of the device in the distal direction during implantation into the tissue. The canted orientation of the rectangular cross-sectional filament still provides the flexibility benefits of the perpendicular orientation discussed above and may enhance anchoring capability by presenting a leading proximal facing edge that serves to grip into tissue.

Barbs formed on the proximally facing edge of the finished implant may be formed on the ribbon prior to winding into its coiled shape. Preferably, the ribbon is formed having barbed shapes along at least one edge of the ribbon by an etching process. A number of ribbons may be etched on a sheet of suitable material, such as stainless steel, at once. After the ribbons are formed on the sheet of material, they may be individually detached from the sheet and wound on a spring winding machine to form a coil by conventional spring winding techniques.

A variety of filament materials may be used such as surgical grade stainless steels. Other materials may be used to vary the modulus of elasticity of the filament. Additionally, flexibility of the coil implant may be varied along the length of the coil, not only by varying spacing between coils and diameter of the filament along its length, but also by using two or more different filament materials along the length of the filament that have different moduli of elasticity.

It is an object of the present invention to provide a tissue implant device that resists migration from the tissue into which it is implanted by offering improved anchoring capability.

It is another object of the present invention to provide a tissue implant device having an anchor mechanism that is easy to integrate into small mechanical devices.

It is yet another object of the present invention to provide an implant device that resists migration by its inherent flexibility and ability to absorb migratory forces exerted by surrounding tissue.

It is another object of the invention to provide an implant device that utilizes an anchoring mechanism that is submerged beneath the surface of the tissue into which the device is implanted.

It is yet another object of the invention to provide a method of implanting a tissue implant device so that it remains anchored in the tissue.

BRIEF DESCRIPTION OF THE DRAWINGS

The foregoing and other objects and advantages of the invention will be appreciated more fully from the following further description thereof, with reference to the accompanying diagrammatic drawings wherein:

FIG. 4 is a side view of a preferred embodiment of the tissue implant device having barbs;

FIG. 5 is a side view of an alternate embodiment of the tissue implant device having barbs;

FIG. 6 is a top view of a sheet of material having a plurality of etched ribbon forms through out its surface.

FIG. 7 is a magnified view of one of the etched ribbon forms on the sheet shown in FIG. 6:

DESCRIPTION OF THE ILLUSTRATIVE EMBODIMENTS

The implant devices of the present invention are particularly useful in treating ischemic tissue such as that which often occurs in a myocardium of the heart. The implant device may be inserted into the myocardium through the epicardial surface at an entry site such that the device extends the majority of the thickness of the myocardium towards endocardial surface.

Figure 1:
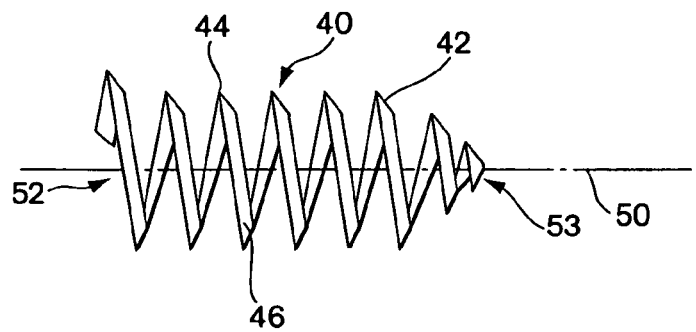
FIG. 1 is a side view of an alternate embodiment of the tissue implant device.
Figure 2:
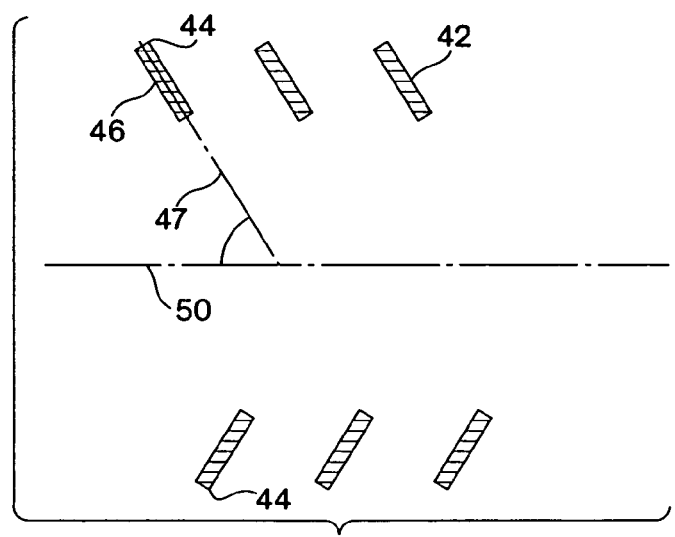
FIG. 2 is a partial sectional view of the tissue implant device shown in FIG. 1.

FIG. 1 shows an embodiment of a tubular implant device. The canted coil device 40 is formed from a filament 42 of rectangular cross-section such as a strand of flat wire. The implant device has a proximal portion 52 and a distal portion 53. As shown in FIG. 2, the coil is formed so that the major cross-sectional axis 47 of the rectangular wire is oriented at an acute angle to the longitudinal axis 50 of the coil 40. The orientation gives each turn 46 of the coil a projecting edge 44, which tends to claw into tissue to serve as an anchoring mechanism for the device.

Figure 3:
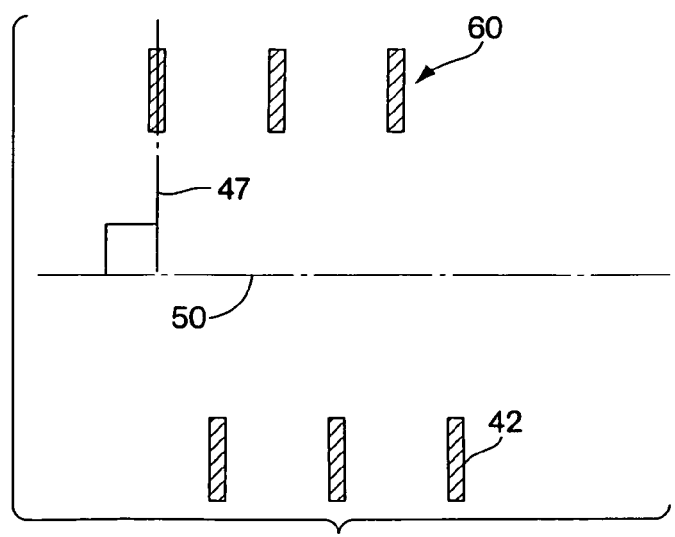
FIG. 3 is a partial sectional view of a variation of the tissue implant device shown in FIG. 2.

FIG. 3 shows a segment of a wrapped ribbon implant embodiment. The implant 60 is formed by a filament of a rectangular cross-sectional filament around a ribbed mandrel. In the present embodiment, the major axis 47 of the rectangular cross-section ribbon is oriented substantially perpendicular to the longitudinal axis 50 of the implant, as is shown in FIG. 3. In this configuration, the major axis 47 of the coils 42 of the rectangular ribbon do not extend radially from the longitudinal axis 50 of the implant 40 at an acute angle. With greater coil surface area extending away from the longitudinal axis of the implant, the implant is believed to be more stable and less likely to migrate once implanted within the myocardium. The implant is preferably formed from 316 stainless steel rectangular cross-section forming wire. Preferred dimensions for the rectangular cross-section filament are on the order of 0.003 inches to 0.005 inches for the minor axis width and 0.015 to 0.018 inches for the major axis.

FIG. 4 shows a preferred embodiment of the wrapped ribbon device 62 having a plurality of barbs 64 formed on the proximally facing edge 63 of the ribbon. The device may only have one barb, but a plurality of barbs is preferred. Each barb has a tapering penetrating shape configured to claw into tissue to resist migration of the device. The barbs may be a variety of shapes such as the curved shape shown in the figures or a sharp pointed shape (not shown). Barbs 64 formed on the spring embodiment shown in FIG. 1 tend to project radially outward from the longitudinal axis of the device at an acute angle, as shown in FIG. 4. The radial projection of the barbs may help to anchor the implant within tissue.

Alternatively, as shown in FIG. 5, the spring device 68 may have coil 70 oriented such that the major axis is parallel to the longitudinal axis of the device and barbs 64 are curved radially outward from the proximally facing edge 72 of each coil 70. The barbs may be curved by bending prior to wrapping of the ribbon into a coil form.

Ribbon material having integrally formed barbs may be formed by variety of methods; however, chemically etching of the ribbon having barbed shapes is preferred FIG. 6 shows a top view of a sheet 76 of material having a plurality of ribbon forms 78 that have been etched through its surface. FIG. 7 shows a magnified view of a single ribbon form 78 comprising a linear ribbon form 79 of a plurality of barb 64, which will ultimately be wrapped into the spring device. Each form 78 remains joined to the sheet 76 after etching by links 77. Ribbon forms are preferably created by a photo etching process. In this process, a photo resistant coating is first applied over the entire sheet of material. Preferably a sheet of stainless steal material is used to having a thickness equivalent to the desired thickness of the final ribbon product as has been defined above. After application of the coating a template having the desired pattern of shapes (a plurality of ribbons having barbs with spare material between each ribbon form) is placed over the sheet. Next light is applied to the sheet to remove the protective coating from areas of the sheet where material is to be removed. The resultant sheet etchant protective coating remains only over areas where material is to remain. The sheet is then exposed to a chemical etchant which removes material from the sheet in the unprotected areas. The resultant 76 sheet shown FIG. 6 has numerous perforations where material has been removed the chemical etchant process provides a quick and economical way to form numerous pieces of ribbon stock having accurately formed barbs. The ribbon forms an easily finished sheet by breaking or cutting links 77. The ribbon may be wrapped in to the helical spring implant device as is described above.

Figure 8A:
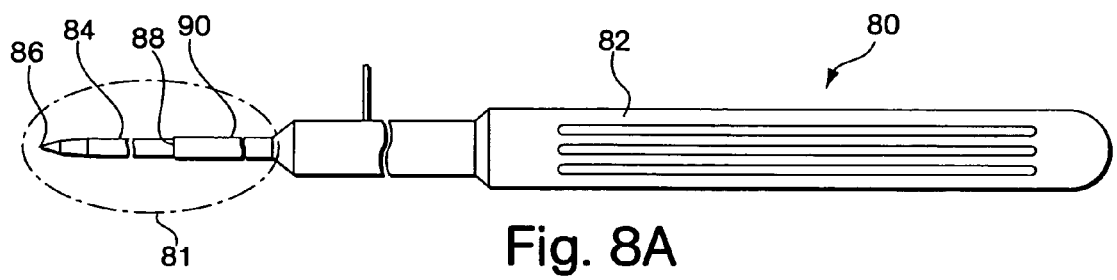
FIG. 8A is a side view of a tissue implant device delivery system.
Figure 8B:
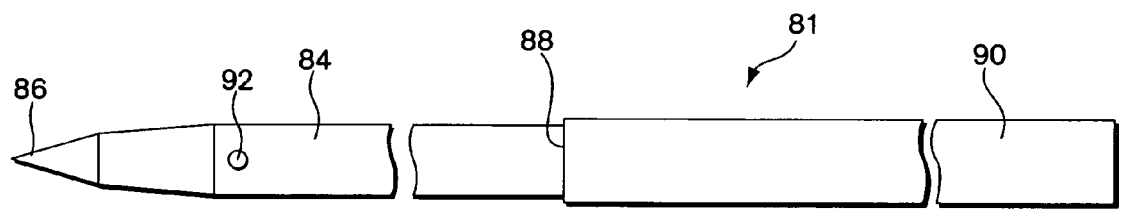
FIG. 8B is a detailed side view of the distal end of the tissue implant device delivery system.
Figure 8C:
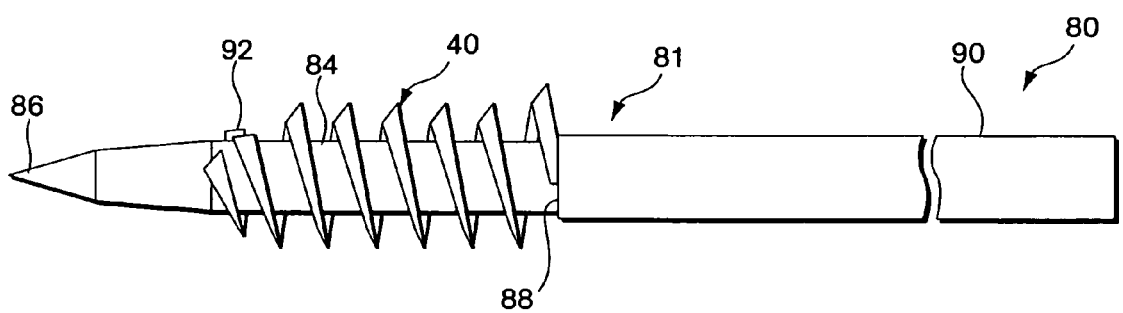
FIG. 8C is a detailed side view of the distal end of the tissue implant device delivery system carrying an implant.

The implant devices of the present invention may be delivered to their intended tissue location surgically. FIGS. 8A–8C show an example of a surgical delivery device that may be used to deliver the implants into tissue such as that of the myocardium of the heart. The delivery device, shown in FIG. 8A, comprises an obturator 80 that includes a main shaft 82, by which it can be gripped and manipulated. The distal end 81 of the shaft 82 is shown in detail in FIG. 8B and includes a reduced diameter device support section 84 having a sharp distal tip 86 adapted to pierce tissue. The diameter of the shaft segment 84 is such as to fit closely within the interior of the devices. The proximal end of the segment 84 terminates in a shoulder 88 formed at the junction of a proximally adjacent, slightly enlarged diameter portion 90 of the shaft. The distal end of the device support segment 84 may include a radially projecting pin 92 dimensioned to project and fit between adjacent turns of the coils of a device. The pin 92 engages the coils in a thread-like fashion so that after the assembly has been inserted into the tissue, the obturator 80 can be removed simply by unscrewing the obturator to free it from the implanted coil. Alternatively, the obturator may be configured without the projecting pin 92 so that the device can be slipped on and off the obturator, without screwing. When an implant device 40 is mounted on the obturator 80, as is shown in FIG. 8C the proximal end of the device may bear against the shoulder 88, and a tail. If so equipped may extend along the segment 90 of the obturator.

In use, the intended tissue location is first accessed surgically, such as by a cut-down method. The obturator, with an implant device loaded on to segment 84, then may be advanced into the tissue to deliver the implant. The sharp tip pierces the tissue permitting the obturator and implant to be pushed inward into the tissue. In the example of delivery to the myocardium, the epicardial surface of the heart is accessed and penetrated by the obturator to deliver the implant. The shoulder 88 prevents proximal movement of the implant along segment 84 during delivery. Preferably, the distal end of the obturator is projected to, and slightly beyond, the endocardium to place the implant device. The obturator then may be unscrewed and separated from the implant device. If the obturator is configured without the pin 92, the obturator may be withdrawn directly from the device and the tissue. Simply applying light closure pressure to the epicardial puncture will cause the puncture hole to clot at the epicardium.

Generally, surgical grade stainless steels are used to fabricate the implant devices discussed above, but other materials having different moduli of elasticity such as nickel titanium alloys can be used.

From the foregoing it will be appreciated that the invention provides a novel approach to providing an anchoring system for implant devices. The devices and methods of the present invention are simple and easy to apply to a wide range of implant designs.

It should be understood however, that the foregoing description of the invention is intended merely to be illustrative thereof and that other modifications, embodiments and equivalents may be apparent to those who are skilled in the art without departing from its spirit.

Having thus described the invention what we desire to claim and secure by Letters Patent is:

1. A tissue implant device configured to resist migration in tissue comprising a ribbon-like filament configured in a flexible helical coil having a plurality of turns, the filament having a flat shape and an integral outer edge along its length, the edge being shaped to define a plurality of outwardly projecting barbs adapted to engage surrounding tissue in which the implant is embedded.

2. An implant as defined in claim 1 wherein the barbs are proximally facing.

3. A tissue implant device as defined in claim 2 wherein the barbs project proximally away from the edge of the coil.

4. An implant as defined in claim 1 wherein each barb has a sharp point configured for engaging tissue.

5. An implant device as defined in claim 1 wherein each turn of the coil has a proximally facing edge and a plurality of barbs projecting from the edge of each turn.

6. A tissue implant device as defined in claim 1 wherein the barbs project radially outward from the edge of the coil at an angle inclined in the proximal direction.

7. A tissue implant device as defined in claim 1 wherein the barbs curve radially outward from the edge of the coil at an angle inclined in the proximal direction.

8. A tissue implant device configured to resist migration in tissue comprising a flexible helical coil having an outer, helical edge shaped to define a plurality of integral outwardly extending barbs, each barb having a rounded contour adapted to engage surrounding tissue.

9. A tissue implant device configured to resist migration in tissue comprising a flexible helical coil having an outer, integral edge shaped to define a plurality of outwardly extending barbs adapted to engage surrounding tissue, the coil being in the form of a flat filament and comprising a plurality of materials each having a different modulus of elasticity.

10. An implant as defined in claim 9 wherein the coil is formed from metal.

11. An implant as defined in claim 10 wherein the metal is stainless steel.

12. A tissue implant device as defined in claim 10 wherein the coil is formed from a nickel titanium alloy.

13. An implant as defined in claim 9 wherein the modulus of elasticity of the coil varies along its length.

14. A method of forming a tissue implant device comprising:
    forming a ribbon from a sheet of material by a photochemical etching process, the ribbon having an edge along its length and a plurality of integral barbs defining the edge;
    separating the ribbon formed from the sheet of material; and
    wrapping the ribbon so formed into a helical coil, plastically deforming the ribbon so that it retains the coil shape with the barbs projecting outwardly of the coil.

15. A method as defined in claim 14 wherein the barbs are formed along an edge that will be proximally facing after the ribbon is wrapped into a coil shape.

16. A method of forming a tissue implant device as defined in claim 14 further comprising forming a plurality of ribbons in a single sheet of material by photochemical etching process.

* * * * *